United States Patent [19]

Brinton, Jr. et al.

[11] Patent Number: 4,801,690

[45] Date of Patent: Jan. 31, 1989

[54] NOVEL LECTINS DERIVED FROM BACTERIAL PILI

[75] Inventors: Charles C. Brinton, Jr.; Mark Hanson, both of Pittsburgh, Pa.

[73] Assignee: Bactex, Inc., Pittsburgh, Pa.

[21] Appl. No.: 842,946

[22] Filed: Mar. 24, 1986

[51] Int. Cl.$^4$ .................. A61K 37/02; A61K 39/108; A61K 39/112; C12N 1/00

[52] U.S. Cl. .................... 530/396; 530/418; 530/825; 424/92; 435/320

[58] Field of Search .................. 424/92; 530/396, 412, 530/418, 823, 824, 825; 435/317

[56] References Cited

U.S. PATENT DOCUMENTS 4,343,792 8/1982 Gouet et al. ..................... 424/92

OTHER PUBLICATIONS

Salit et al., Journal of Experimental Medicine 146, pp. 1160–1181 (1977).

Eshdat et al., Biochemical and Biophysical Research Communications 85 (4), pp. 1551–1559 (1978).

Olafson et al., Infection and Immunity 48(2), pp. 336–342 (1985).

Matsui et al., Journal of Biochemistry 97, pp. 399–408 (1985).

Sharon et al. CIBA Foundation Symposium 80, pp. 119–141.

Eshdat et al, Methods in Enzymology 83, pp. 386–391 (1982).

*Primary Examiner*—John Edward Tarcza
*Attorney, Agent, or Firm*—Omri M. Behr

[57] ABSTRACT

A lectin derived from the pili of piliated organisms, said lectin being non-covalently bindable to the pilus rod protein of said pili and separable therefrom by the action of aqueous sodium dodecyl sulfate, possessing a single binding site for binding to mammalian erythrocyte ghosts.

16 Claims, 4 Drawing Sheets

NOVEL LECTINS DERIVED FROM BACTERIAL PILI

BACKGROUND OF THE INVENTION

It has been known for many years that the pili of piliated pathogenic organisms play an important role in the pathogenicity of these organisms. It has been shown that these pili adhere to erythrocytes and similar cells whereby the bacteria are attached thereto. The mechanism by which pili adhere to erythrocytes and the like has also been long studied. It is believed that the adhering mechanism involves a particular protein which has an affinity for a particular group or groups on the surface of mammalian cells. Heretofore, it has been believed that the adhesion is a moiety which is part of the pilus rod protein.

SUMMARY OF THE INVENTION

A lectin which is derived from the pili of piliated organisms which is non-covalently bound to the pilus rod protein has been isolated. Lectins are proteins having a carbohydrate specific binding site (Ann. Rev. Plant Physiol. 27, 291 (1976)). They are subdefined by their origin, i.e., zoolectins or phytolectins. The subject matter of the present invention is a new sub-group, i.e., bactolectins (derived from bacteria). This lectin interacts mono-valently with sugar sites such as mannose sites on the surface of mammalian cells. The term monovalent in this context means that there is only one binding site for each lectin. The lectin is one of several minor protein components of the pili themselves. Among the organisms which possess such lectins may be named *Escherichia Coli*, in particular Type I *E. Coli*, *Pseudomonas Aeruginosa*, *Bordatella Bronchiseptica*, *Moraxella Bovis*, *Salmonella Species*, *Haemophilus Influenzae*, *Moraxella Catarrhalis*, *Neisseria Gonorrhea*, *Neisseria Meningitidis*, *Klebsiella Pneumoniae*, *Bordatella Pertussis* and *Streptococcus Pneumonae*. The lectins have a molecular weight of between about 25 to about 50 kilodaltons (Kd), suitably between 27 and 35 Kd. The binding site which is responsible for adhesion to the aforesaid sugar moiety on the mammalian cells is, for certain lectins, deactivable by aqueous papain in the presence of urea provided that the urea concentration is at least 4M. Where the urea concentration is less than 4M, very little denaturation takes place and even at concentrations of 8M urea, there is no denactivation in the absence of papain.

In order to produce the lectins of the present invention substantially pure pili are produced. These pili are then digested with a detergent, suitably sodium dodecyl sulfate or sarkorsinate at a concentration of between about 2 to about 5 wt. % and a pH of about 7 to about 9. The pili are then digested. It is preferred to carry out the digestion in two stages. In the first stage, it is carried out at between about 20° to about 40° C. after which the undissolved material is removed, the aqueous residue discarded and the said undissolved material redissolved in a similar solution and redigested at a higher temperature, suitably between about 80 and 100° C. The remaining undissolved material is again removed, suitably by centrifuguation, preferably at at least 10,000 g., suitably up to about 100,000 g. The aqueous material is again preserved. The proteinaceous material in these aqueous solutions is then precipitated. Suitably, the precipitant is a 10-20 vol/vol of a water soluble organic solvent such as an alkyl ketone, suitably acetone; a carboxylic acid such as acetic acid; or a tertiary amine such as trialkylamine. The precipitate is then separated, washes with suitable solvent, and redissolved in the aforesaid detergent solution but at a lower concentration, suitably between about 0.5 and 2 wt. % (SDS).

The proteins in this solution are then resolved by well known procedures such as gel filtration chromatography or acrylamide gel electrophoresis and the desired lectin, having a molecular weight as stated hereinabove, is isolated. The lectins constitute approximately 1% by weight of the protein content of the pili. It has been found that the lectins derived from *E. coli* Type I pili and from Salmonella Type I pili are D-mannose specific.

BRIEF DESCRIPTION OF THE DRAWINGS

FIG. I is a photograph of an SDS acrylamide gel chromatogram of the depolymerized pili of Table 1.

FIG. II is a photograph of an SDS acrylamide gel chromatogram of products of Example V.

DESCRIPTION OF THE PREFERRED EMBODIMENTS

Figure 1:

In preparing the lectins of the present invention it is desirable to start with substantially pure pili, free from other contaminants. In the preferred mode, piliated bacteria are grown on rich solid medium and are suspended in 0.15M aqueous saline prior to blending, suitably at about 10,000 rpm for from about 1 to about 5 minutes. The supernatant of the centrifugation is preserved and separated from the precipitated cells. The pili in the supernate are aggregated by addition of a suitable salt, for example, 0.1M magnesium chloride, and are purified by alternating cycles of crystallization and solubilization to remove soluble and particulate debris respectively.

The piliated organisms can be grown in a fairly wide temperature range, for example, between about 20° and about 40° C. While magnesium chloride is preferred as the precipitating agent, calcium chloride, sodium chloride, potassium chloride or ammonium sulfate of at least 5% saturation or more may be utilized.

It has been found that the pili maintain their integrity under mild detergent conditions. Thus, the pili suspended in an alkaline buffer, suitably from between 7 to about 9, with between 2 to 5% of detergent, suitably sodium dodecyl sulfate or sarkosinate. Dithiothreitol (up to 50 mM, preferably 5 to 10 mM) may be added to aid solubilization. The suspended pili are mixed in the solution at a temperature of between about 20° to about 37° to ensure dispersal of all the clumps of material. The pili are then sedimented by centrifugation, suitably at about 10,000 g or greater. This procedure ensures removal of undesired soluble contaminants.

Occurrence of Pilus-Associated Proteins

*E. Coli* Type I pili were purified from 20 different strains (numbers 1-19 courtesy of H. J. Cho). Concentrations range from 0.36 mg/ml to 2.46 mg/ml. Pili were depolymerized (pH 2/100°), run on SDS-PAGE and silver stained. Order of strains is as given in Table 1. The position of the 28 Kd band is indicated in FIG. I. Lane 21 contains MW standards.

TABLE 1

Hemagglutinating Activities within the Type I Family

| Strain/Clone | HA Endpoint Conc. (ug/ml) | Sero-Type | Isolate Source |
|---|---|---|---|
| (1) SP9/001 | 24 | II | Porcine enterotoxigenic |
| (2) SP13/001 | 2 | II | " |
| (3) SP14/001 | 36 | II | " |
| (4) SP16/001 | 25 | II | " |
| (5) H10401/001 | 2 | ND(a) | Human enterotoxigenic |
| (6) H10401/003 | 25 | ND | " |
| (7) H10407 | 2 | IV | " |
| (8) H13634/001 | 3 | IV | Human enteroinvasive |
| (9) B44/001 | 36 | II | Bovine enterotoxigenic |
| (10) Br1l/001 | 13 | X | Human pyelonephritic |
| (11) Br0111/001 | 3 | II | " |
| (12) AW405 | >230 | ND | Lab. (J. Adler) |
| (13) C9/001 | 91 | VIII | Human cystitic |
| (14) PS/001 | 49 | II | Porcine enterotoxigenic |
| (15) 27052/001 | 13 | IX | Human ABU[b] |
| (16) 1676/003 | 36 | I | Porcine enterotoxigenic |
| (17) 1459/003 | 3 | XIII | Bovine enterotoxigenic |
| (18) 190/103 | 25 | II | Porcine enterotoxigenic |
| (19) SP27/005 | 25 | II | " |
| (20) BAM | 2 | I | Lab. (E.Kellenberger) |

The aggregated pili from the centrifugation are again resuspended in the detergent at a concentration exceeding 1 mg/ml. It is preferred that a concentration of between 5 to about 10 mg/ml is attained. The solution is then heated to a temperature of at least about 80°/C. up to 100° C. for at least 2 minutes, a 5 minute digestion at 100° C. being preferred. This procedure removes all noncovalently bound proteinaceous material from the pili, leaving pure pilin rods which are then removed by centrifugation at least 10,000 g, suitably up to 100,000 g. In order to avoid precipitation of the detergent, it is preferable to keep the temperature in the range of about 10° to about 20° C. The pellet is then washed, suitably with water or a low strength buffer and the foregoing digestion step is repeated if desired, to obtain purified pilin rods. It is preferable to add protease inhibitors, such as diisopropyl fluorophosphate, phenylmethyl sulphonyl fluoride, etc., to the supernatant, if it is to be stored for more than about 12 hours. The preferred storage temperature is between about 4°.

The last small fragments of rods and rod aggregates may be removed from the supernatant, suitably by filtration (pore size 0.45 um or less) at a temperature suitably between about 20° to about 25° C. to prevent precipitation of the detergent.

The soluble proteins are then precipitated with organic solvents. These solvents are water soluble organic solvents such as lower (1 to 5 atoms) alkyl ketones suitably acetone, lower carboxylic acids suitably acetic acid or tertiary alkyl amine compounds, suitably trimethyl or triethyl amine or mixed solvents such as chloroform/methanol. The thus formed precipitate of minor non-covalently linked proteins is collected, washed in the precipitating solvent, and redissolved in a more dilute solution of the foregoing detergent, suitably at a concentration of between about 0.5 to about 2 wt. %. It is preferred that solution of the proteins be assisted by brief heating suitably from about 2 to about 5 minutes and between 80° to about 100° C.

Resolution of the thus resolved proteins may be carried out by any suitable method. It has been found that resolution may be achieved by chromatography on gel filtration media of fractionation range between about 10,000 to about 100,000 d (media such as Sephadex G75, G100, Biogel P100 or P150, Ultragel ACA54, ACA44 or equivalent media may be employed). Chromatography is carried out using low concentration alkaline SDS/DTT buffer (0.05 to about 0.5 wt. % SDS). Again, it is preferred that the temperature be high enough (i.e., about 20° to about 25° C.) to prevent precipitation of the detergent. Alternatively, the proteins may be resolved by preparative scale SDS polyacrylamide gel electrophoresis wherein the protein bands are visualized, cut out, and the protein eluted from the gel slices. The band visualization may also be obtained by staining, for example with Coomassie Blue in methanol acetic acid or by SDS precipitation with salts such as sodium acetate or potassium chloride. In this procedure, soaking the gel in between 0.25M and 1.0M potassium chloride is preferred. After brief soaking in water to remove the staining solvents or salts, the protein is removed from the slice by electro elution in an SDS buffer of ionic strength about 0.1M or maceration and diffusion into a solution of SDS (1 to 10% wt/vol).

Finally, the precipitated proteins may also be resolved by HPLC by previously suspending them in a suitable ion pairing type solvent (0.5 to 0.05% trifluoroacetic acid is preferred). Separation is carried out by reverse phase chromatography on a suitable hydrophobic interaction column and by elution with an organic solvent gradient in water, for example, 0 to 100% acetonitrile.

The fragments collected in the buffered detergents may be dialyzed at low concentration salt solution (sodium chloride, potassium chloride or potassium phosphate are especially suitable at 0.05 to 0.15M), followed by dialysis to remove salts, dyes and higher amounts of SDS resulting from the purification of these proteins. Those proteins having a molecular weight between 25 and 50 Kd represent the desired fraction, which is preserved.

Characterization of the Adhesion Protein

It is an interesting observation that while crystalline (i.e., aggregated) pili cause hemagglutination of erythrocytes, erythrocyte ghosts and other vertibrate host cells, single rod pili do not cause hemagglutination. Nevertheless, when erythrocytes are exposed to single rod pili (i.e., pilin rod associated with its minor proteins) or when polystyrene latex beads coated with a sugar, such as D-mannose are exposed to single pilus rods and then examined either by exposure to electron microscope or in a high powered optical microscope, it is observed that the single rod pili will adhere at a location proximal to one end thereof to the aforesaid erythrocyte ghosts or the mannose treated polystyrene beads. Interestingly however, it has been observed that when these adhered single rod pili are exposed to anti-pilus rod antiserum containing antibodies to the pilus rod itself, hemagglutination will immediately occur since a cross-linking between the individually adhered pilus rods will take place.

Further evidence for the binding property of the lectins of the present invention comes from observations of a mutant strain of *E. Coli* Type I pili (Strain K12-AW405) (Collection of the Department of Microbiology, University of Pittsburgh, Charles C, Brinton, Source—J. Adler) which when grown at 37° C. or above was found to produce pili which had no detectable hemagglutinating activity with respect to erythrocyte ghosts. When subjected to the detergent digestion procedures of the present invention, it was found that this strain, while having minor proteins, was lacking a protein in the 25 to 50 Kd range.

It has been found that the adhesion quality of certain single rod pili can be deactivated by the action of papain in urea. Unless the urea concentration exceeds 4M, only negligible deactivation will occur. On the other hand, no deactivation will occur if papain is absent up to a concentration of 8M urea. None of the minor proteins isolated in the foregoing detergent digestion will cause hemagglutination. Furthermore, none of these proteins except for the lectin will adhere to erythrocyte ghosts. Similarly, the adhesive interaction between the native pilus associated lectin and the erythrocytes can be prevented by treatment of the un-adhered lectins with antilectin antibody.

The thus produced lectins have many uses due to their carbohydrate specificity. They can be bound to such substrates as polystyrene gel by conventional procedures such as treatment with cyanogen bromide, whereby they can serve as affinity substrates for the purification of specific carbohydrates from complex mixtures, for example, the *E. Coli* and Salmonella Type I pili, being mannose specific may be utilized for the isolation of mannose from mixtures containing same. Similarly, monoclonal antibodies to the lectins may be prepared which in turn are used to generate anti-idiotype antibodies, which in turn can be used as anti-idiotype vaccines in order to generate specific idio types to the tip adhesion proteins within the system to which they are administered. Furthermore, it is possible to attach markers to the lectins which lectins are then utilized as biosensors for the detection and assay of predetermined carbohydrates such as mannose.

The procedures of the present invention which involve mild detergent digestion of the pili make possible the removal from single rod pili of lipopolysaccharides associated therewith. This is an important development in the manufacture of whole pilus vaccines as the lipopolysaccharides cause antigenic reactions without immunizing benefit.

The procedures also make possible, by the more vigorous digestion with detergent, the production of pure pilin rods which are useful as a diagnostic tools for the characterization of pilus families by procedures such as the ELISA assay.

EXAMPLE I

Purification of Pili

*E. Coli* Type I piliated bacteria (ATCC 67053, Strain Bam; Collection of Department of Microbiology, University of Pittsburgh, Charles C. Brinton—Source E. Kellenberger, Geneva, Switzerland (1954)) are grown on rich solid medium in the conventional manner at a temperature within the range of 22° to 37° C. The bacterial growth is then suspended in aqueous sodium chloride (0.15M) and blended (10,000 rpm, 2 minutes). The product is then centrifuged at 10,000 g, the residual debris removed and the solubilized pili aggregated by the addition of aqueous magnesium chloride (0.1M). The aggregated pili are then precipitated by similar centrifugation and the supernatant discarded. The foregoing solution/precipitation cycle is repeated at least three (3) times to obtain substantially pure *E. Coli* Type I pili. Pili (100 mg) are suspended in SDS (40 ml, 4% w/w), dithiothreitol (10 mm), pH 8 and agitated for 15 min at 25° C., followed by centrifugation at 10,000 g.

The residue comprises pili substantially free of lipopolysaccharide contaminants.

EXAMPLE II

In accordance with the above procedure but in place of utilizing *E. Coli*, there may be utilized *P. Aeruginosa, B. Bronchiseptica, M. Bovis,* Salmonella Species, *H. Influenzae, M. Catarrhalis, N. Gonorrhea, N. Meningitidis K. Pneumoniae, B. Pertussis* or *S. Pneumoneae.*

EXAMPLE III

*E. Coli* Type I pili 200 mg. were suspended in an aqueous solution of sodium dodecyl sulfate (4%, 10 ml) containing 10 mM dithiothreitol (DTT), and 10 mM tris at pH 8 and boiled for 5 minutes. The mixture was cooled to between 20° and 25° C. and sedimented by centrifugation at 100,000 g for 1 hour to yield the SDS aggregated pilin rods as the precipitate.

The supernatant contains the three minor proteins having molecular weights of approximately 28 Kd, 16.5 Kd and 14.5 Kd as shown by SDS polyacrylamide electrophoresis.

EXAMPLE IV

Separation of Minor Proteins

Figure 2:
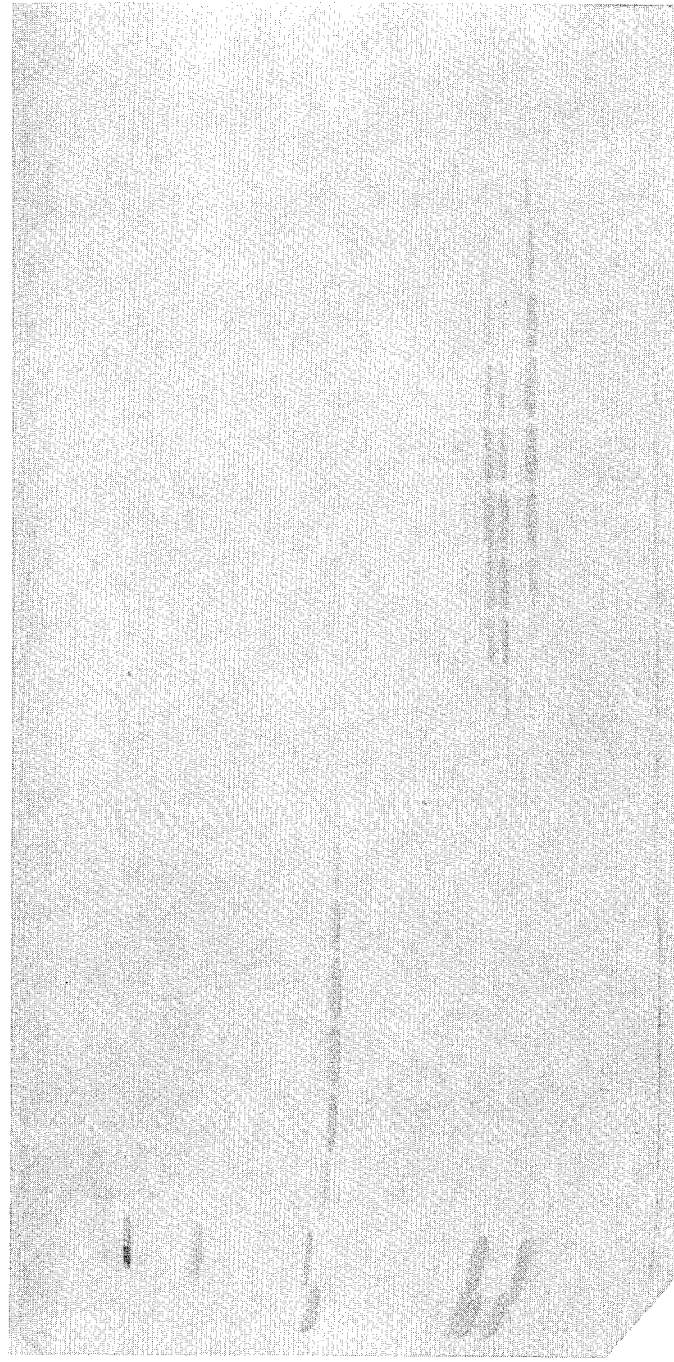
Figure 3:
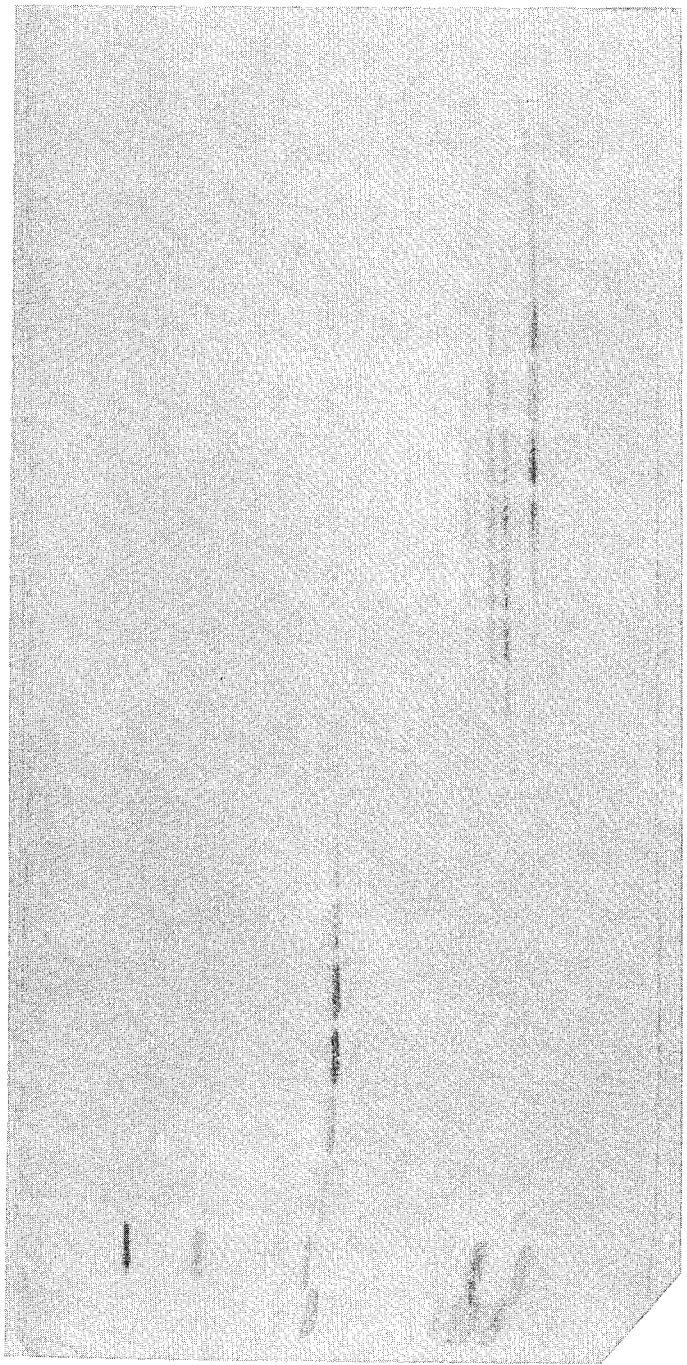
Figure 4:

The aqueous solution containing the proteins from the previous Example was treated with acetone (100 ml). Whereby the proteins were precipitated, the mixture centrifuged at 10,000 g. for 15 minutes, the supernate discarded and the precipitate resuspended in SDS solution (1%, 10 ml) containing 10 mM tris, 1 mM dithiothreitol at pH 8. The mixture was loaded onto a Sephadex G75 column (1.5 by 110 cm) and the proteins eluted with a similar buffer of SDS (0.1%). Flow rate was 8 ml/hr. and 1 ml fractions were collected. Gel chromatography (FIG. 2) showed that the 28 Kd protein was located principally in fractions 3 thru 8, starting at the void volume.

The fractions were pooled and acetone precipitated as above.

EXAMPLE V

In accordance with the above procedure but in place of utilizing *E. Coli*, there may be utilized *P. Aeruginosa, B. Bronchiseptica, M. Bovis,* Salmonella Species, *H. Influenzae, M. Catarrhalis, N. Gonorrhea, N. Meningitidis, K. Pneumoniae, B. Pertussis* or *S. Pneumoneae* to yield a similar lectin.

TABLE 2

| | Amino Acid Analysis of Pilus Associated Proteins Obtained in the Foregoing Experiments | | | | |
|---|---|---|---|---|---|
| Amino Acid | 37518 Rod Subunit 20.5 Kd # RES | BAM Rod Subunit 17 Kd # RES | 37518 14 Kd # RES | 37518 33 Kd # RES | BAM 28 Kd # RES |
| ASP | 24 | 20 | 18 | 41 | 32 |
| THR | 28 | 20 | 14 | 25 | 26 |
| SER | 18 | 10 | 8 | 23 | 24 |
| GLU | 13 | 13 | 11 | 25 | 17 |
| PRO | 11 | 2 | 7 | 21 | 16 |
| GLY | 14 | 17 | 17 | ND | ND |
| ALA | 34 | 34 | 18 | 25 | 25 |
| CYS (½) | 3 | 2 | ND | ND | ND |
| VAL | 14 | 13 | 7 | 30 | 29 |
| MET | 1 | 0 | 0 | 2 | 0 |
| ILE | 7 | 4 | 5 | 13 | 12 |
| LEU | 12 | 10 | 12 | 18 | 17 |
| TYR | 3 | 2 | 3 | 13 | 15 |
| PHE | 7 | 8 | 4 | 14 | 9 |

TABLE 2-continued

Amino Acid Analysis of Pilus Associated Proteins Obtained in the Foregoing Experiments

| Amino Acid | 37518 Rod Subunit 20.5 Kd # RES | BAM Rod Subunit 17 Kd # RES | 37518 14 Kd # RES | 37518 33 Kd # RES | BAM 28 Kd # RES |
|---|---|---|---|---|---|
| HIS | 1 | 2 | 1 | 2 | 2 |
| LYS | 9 | 3 | 5 | 13 | 6 |
| ARG | 4 | 3 | 4 | 14 | 8 |
| TRP | ND | 0 | ND | ND | ND |
| TOTAL | 203 | 163 | 134 | 279 | 238 |
| MW | 20540 | 17000 | 13600 | 33200 | 28000 |

Amino acid analysis data of pilus-associated proteins from strain *Salmonella Newport* #37518 and *E. Coli* Type I strain BAM.

EXAMPLE VI

Papain Inactivation of Pili

Pure pilus rods (crystalline) pili were resuspended to 0.5 mg/ml in 50 mM NaCl, 10 mM tris, 10 mM cysteine-HCl, 5 mM EDTA, pH 7.4 with various concentrations of urea. A freshly prepared solution of papain in water was added to half of each pili-urea suspension to a final pili:papain ratio of 25:1 (wt:wt). The remaining half received no papain. The pili (0.5 ml) in urea with or without papain were incubated at 37° for 1 hour, then placed in individual dialysis sacs and dialyzed extensively against distilled water. The evidence of proteolysis was judged by SDS-PAGE of depolymerized and undepolymerized papain-treated pili.

Papain treatment had no effect on any protein associated with whole pili unless urea was present in excess of 4M. In these samples, only the 28 Kd band, is lost. No degradation of any band occurs in 8M urea in the absence of Papain.

The relative adhesion activity of papain/urea-treated pili was determined by passive hemagglutination (HA). Dialyzed soluble pili were two-fold serially diluted in phosphate buffered 50 mM NaCl containing 4% sorbitol. An equal volume of 2% guinea pig blood was added, the mixture incubated 30 minutes, then added to an equal volume of 1:100 anti-whole pilus serum. Relative HA strength is expressed as the titration endpoints. Treating pili with urea at 0 to 8M in concentration in the absence of papain had little effect on HA activity. The activity of pili incubated with papain was unaffected at concentrations of urea less than 4M, but decreased to negligible levels at urea concentrations of 4M or above when the enzyme was present. Though no attempt was made to eliminate residual papain activity in the HA assay, control experiments showed that results from assays to which active papain was deliberately added were identical to those without added enzyme.

EXAMPLE VII

Coupling of 28 Kd Lectin to Solid Carrier Beads for Use as Mannose Receptor Specific Probe One Hundred (100) mg. of lectin derived from *E. Coli* Type I (strain Bam) prepared in accordance with Example IV is mixed with 10 ml. of CNBr Sepharose Gel (Pharmacia.) in a mixture of 0.1M $NaHCO_3$ and 0.5M NaCl at pH 8.3. The mixture is agitated gently for 2 hours at ambient temperature and the unreacted CNBr groups blocked with 1M ethanolamine for 2 hours at ambient temperature. The excess unbound protein is washed away with coupling buffer followed by 0.1M acetate buffer (pH 4) containing 0.5M NaCl. After washing again with coupling buffer to remove excess blocking agent, the lectin conjugated Sepharose is utilizable as a probe for materials containing mannose specific receptor sites.

We claim:

1. A bactolectin derived from the pili of an organism selected from the group consisting of *E. coli*, and Salmonella Species, said lectin being non-covalently bindable to the pilus rod protein of said pili and separable therefrom by the action of hot aqueous sodium dodecyl sulfate and possessing at least a single binding site for binding to mammalian erythrocyte ghosts.

2. A lectin of claim 1 whose binding site to mammalian erythrocyte ghosts is inactivable by the action of aqueous papain in the presence of urea at a concentration of at least 4M but being substantially unaffected by papain at lower urea concentrations and substantially unaffected by aqueous urea in the absence of papain at concentrations of less than 8M.

3. A lectin of claim 1 wherein the organism is *E. Coli* Type 1 or *S. Newport*.

4. A lectin of claim 3 having a molecular weight of about 28 Kd derived from *E. Coli*.

5. A lectin of claim 3 having a molecular weight of about 33 Kd derived from *S. Newport*.

6. A lectin of claim 1 having a molecular weight of between 25 Kd and 50 Kd.

7. A lectin of claim 1 having a molecular weight of between about 27 and 35 Kd.

8. A process for isolating a lectin of claim 1 from substantially pure pili which comprises:
    (a) suspending said pili in an aqueous solution of a detergent at a concentration of about 5 to about 2 wt % at pH of about 7 to about 9,
    (b) digesting said mixture at between about 20° about 40° C.,
    (c) removing undissolved material from said mixture,
    (d) discarding the aqueous phase of (c),
    (e) redissolving said undissolved material in an aqueous solution as in (a) above,
    (f) digesting said mixture at between about 80° and about 100° C.,
    (g) removing undissolved material from said mixture,
    (h) precipitating dissolved proteinaceous material from the preserved aqueous phase of (g) by the addition of a water soluble alkanol, alkyl ketone, carboxylic acid or tertiary amine solvent,
    (i) separating said precipitate, and redissolving same in an aqueous solution as in (a) above at a concentration of between about 0.5 and about 2 wt%,
    (j) resolving said proteins and isolating the fragments having molecular weight between about 25 and about 50 Kd.

9. A process of claim 8 wherein the detergent is sodium dodecyl sulfate or sarkosinate.

10. A process of claim 8 wherein the solvent is chloroform/methanol, acetone, acetic acid or triethylamine.

11. A process of claim 8 wherein the precipitates are separated by centrifugation of at least 10,000 g.

12. A process of claim 8 wherein the precipitates are separated by centrifugation of up to about 100,000 g.

13. A process of claim 8 wherein the protein is resolve by gel filtration chromatography.

14. A process of claim 8 wherein the protein is resolved by polyacrylamide gel electrophoresis.

15. A process for purifying single rod pili of an organism selected from the group consisting of *E. coli*, and Salmonella Species, by removing therefrom at least lipopolysaccharides generally associated therewith while maintaining the association therewith of other proteins normally associated therewith with comprises
  (a) suspending said pili in an aqueous solution of a detergent at a concentration of about 5 to about 2 wt % at pH of about 7 to about 9,
  (b) digesting said mixture at between about 20° and about 40° C.
  (c) removing and preserving the undissolved material consisting essentially of pure single rod pili from said mixture.

16. A process for isolating pure pilin from substantially pure pili of an organism selected from the group consisting of *E. coli*, Salmonella Species, which comprises
  (a) suspending said pili in an aqueous solution of a detergent at a concentration of about 5 to about 2 wt % at pH of about 7 to about 9,
  (b) digesting said mixture at between about 20° and about 40° C.,
  (c) removing undissolved material from said mixture,
  (d) discarding the aqueous phase of (c),
  (e) redissolving said undissolved material in an aqueous solution as in (a) above,
  (f) digesting said mixture at between about 80° and about 100° C.,
  (g) removing and preserving the undissolved material consisting essentially of substantially pure pilin from said mixture.

* * * * *